July 17, 1962 W. R. TUCKER Plant Pat. 2,156
PECAN PLANT
Filed Oct. 21, 1960
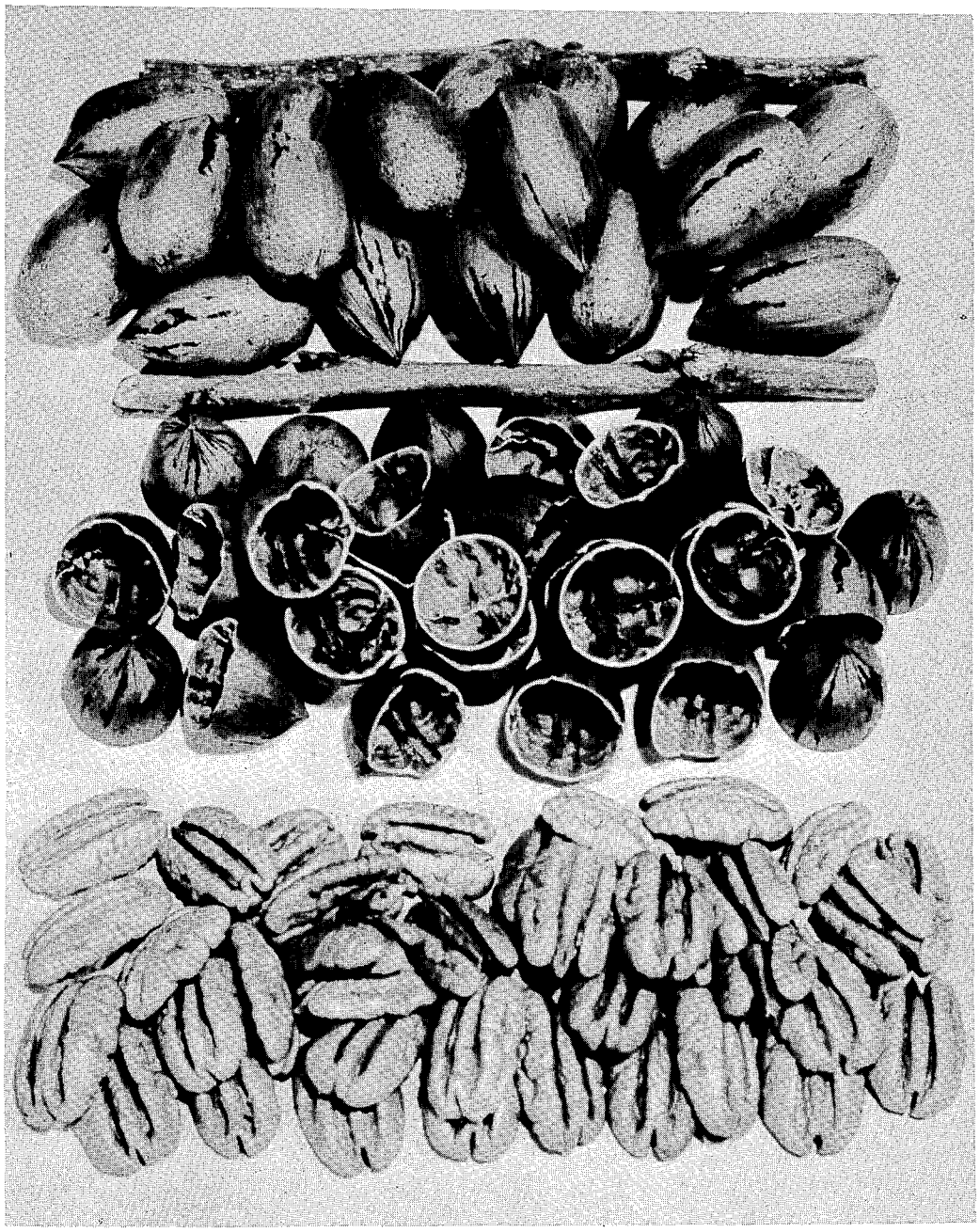
INVENTOR
William R. Tucker United States Patent Office Plant Pat. 2,156
Patented July 17, 1962

2,156
PECAN PLANT

William R. Tucker, Dawsonville, Ga.

Filed Oct. 21, 1960, Ser. No. 64,231
1 Claim. (Cl. 47—62)

This invention relates to a new and distinct variety of pecan tree, the same being a hybrid between Schley (unpatented) and Stuart (unpatented), Schley being the pollen parent and Stuart being the seed parent; the cross-breeding of these two standard varieties of pecans resulting from dusting the pollen of Schley onto the pistillate flowers of Stuart.

About 250 selected Stuart nuts, thus cross-pollinated, were planted during the months of February and March of each of three consecutive years—ample space being given between seed-nuts for the rapid growth of the resulting young trees; and these young hybrid trees were fertilized, cultivated and cared for until they came into bearing.

Upon attaining bearing age each young tree was minutely examined, both with regard to the tree and also to the nuts which it bore; and from such detailed examination it was found that of all the approximately 678 young trees involved in this experiment only one possessed all of the desired qualities of both Schley and Stuart, with none of the objectionable features of either; and this one unusual tree, now growing here in Dawson County, Georgia, constitutes the basis of my invention.

Asexual reproduction of my new variety of pecan by budding and grafting has been performed for me at a pecan nursery near Albany, Georgia; and the owner and operator of this nursery, who is regarded as a pecan expert in the Albany area, has just completed a six-year test to determine which of the fifteen varieties of pecans tested are most resistant to scab in that area.

My new variety was one of the fifteen varieties of pecans tested, and the other fourteen varieties were Alley, Champion, Delmas, Desirable, Elliott, Farley, Mahan, Mobile, Moneymaker, Moore, Pabst, Schley, Stuart and Van Deman. This test, conducted by a disinterested pecan expert, showed that my new variety and only four of the other varieties tested were satisfactorily resistant to scab.

A recent inspection of some 40 young trees of my new variety now growing in the Albany area, while failing to disclose any scab or other pecan disease, clearly showed that the limbs, foliage and nuts of these young asexually propagated trees are exact duplications, respectively, of the limbs, foliage and nuts of the original parent tree here in Dawson County.

Referring to the accompanying illustration:

(1) It is seen from the twigs shown that my new variety has clean healthy wood, and well developed buds.

(2) The group of whole nuts shown gives an accurate idea of the outward appearance of my new variety.

(3) The row of shells shown illustrates (*a*) the thinness of shell; (*b*) the clean, smooth rounded voids formerly occupied by the kernels; and (*c*) the uniformity with which the shells can be transversely broken in halves and the kernels extracted in whole form.

(4) And the bank of kernels shown evidences the fact that the kernels of the pecans of my new variety of pecan tree are exceptionally full, clean, smooth and of uniform size and shape.

Description of my new variety more in detail:

*As to Tree*

*Size.*—Large.

*Disease resistance.*—To date no sign of scab or other pecan disease. Was one of five varieties showing satisfactory resistance to scab in the Albany, Georgia, area, in a six-year test involving my new variety and fourteen other well known varieties of that area.

*Productivity.*—Very productive.

*Growth habit.*—Vigorous and fast growing.

*Limbs.*—Medium to heavy.

*Foliage.*—Abundant and relatively large.

*Buds.*—Pointed and well developed.

*As to Nuts*

*Size.*—One and five-eighths to one and three-fourths inches long, ond three and one-eighth to three and three-fourths inches in circumference.

*Shape.*—Similar to Stuart, but slightly more pointed at the apex.

*Shell.*—Somewhat thicker than Schley, but definitely thinner than Stuart.

*Weight.*—About forty-four to the pound.

*Maturity.*—Complete maturing and filling.

*Cluster.*—Three, four, five and six nuts to the cluster.

*Harvesting season.*—The last half of November in the Albany, Georgia, area; or approximately fifteen days later than Stuarts of the same locality.

*Kernels.*—Fine textured, smooth and uniform in size and shape.

*Oil content.*—More oil than moisture; and while drying the kernels of my new variety shrink uniformly, like the kernels of the Schley variety; instead of forming hollow spaces inside, as do the kernels of the Stuart variety.

*Shelling properties.*—Excellent.

*Taste.*—Excellent. More like that of Schley than that of Stuart, but superior to that of either.

I claim:

A new and distinct variety of pecan tree, substantially as herein shown and described, the same being a hybrid whose pollen parent was a Schley and whose seed parent was a Stuart; characterized as to novelty that the tree is scab resistant, vigorous and fast growing, with an abundance of relatively large foliage; and the nuts of which outwardly resemble Stuart but inwardly are more like Schley, and which nuts are particularly distinguished as to novelty by their unusual weight, their complete maturing and filling properties, their excellent shelling qualities, the lateness of their harvesting season; the texture, plumpness and smoothness of their kernels; their high oil content and their excellent taste.

No references cited.